United States Patent [19]

Tiwari

[11] Patent Number: 4,882,032
[45] Date of Patent: Nov. 21, 1989

[54] HYDROGEN PROBE

[75] Inventor: Basant L. Tiwari, Sterling Heights, Mich.

[73] Assignee: General Motors Corporation, Detroit, Mich.

[21] Appl. No.: 211,606

[22] Filed: Jun. 27, 1988

[51] Int. Cl.$^4$ ............................................. G01N 27/46
[52] U.S. Cl. .................................. 204/422; 204/1 T; 204/426
[58] Field of Search ....... 204/1 S, 1 H, 1 T, 421–429, 204/433

[56] References Cited

U.S. PATENT DOCUMENTS

| | | | |
|---|---|---|---|
| 3,410,780 | 11/1968 | Holden | 204/426 |
| 3,679,551 | 7/1972 | Kolodney | 204/433 |
| 3,727,058 | 4/1973 | Schrey | 204/426 |
| 3,960,693 | 6/1976 | Weyl et al. | 204/428 |
| 4,007,106 | 2/1977 | Hone et al. | 204/422 |
| 4,065,371 | 12/1977 | Rodgers et al. | 204/433 |
| 4,088,543 | 5/1978 | Ruka | 204/428 |

OTHER PUBLICATIONS

R. Gee and D. J. Fray, *Instantaneous Determination of Hydrogen Content in Molten Aluminum and Its Alloys*, Metal. Trans., vol. 9B, Sep. 1978, pp. 427–430.

G. J. Licina, P. Roy and C. A. Smith, "*Mat. Behav. Phys. Chem. Liq. Met., Sys.*", Edited by H. Borgstedt, Plenum Press, New York (1982), pp. 297–307.

P. D. Hess, *Light Metals*, The Metallurgical Society of AIME, (1972), pp. 367–385.

*Primary Examiner*—T. Tung
*Attorney, Agent, or Firm*—Lawrence B. Plant

[57] ABSTRACT

Probe for the electrochemical determination of the hydrogen content of molten aluminum comprising: a catalytic metal membrane hydrogen electrode; a Ca-CaH$_2$ counterelectrode; a solid-state electrolyte such as calcium hydride, calcium hydrochloride and strontium hydrochloride; a porous barrier separating the aluminum from the hydrogen electrode; and a hydrogen accumulation chamber adjacent the catalytic membrane.

4 Claims, 2 Drawing Sheets

HYDROGEN PROBE

This invention relates to a probe for electrochemically determining the hydrogen content of molten aluminum.

BACKGROUND OF THE INVENTION

It is well known that the hydrogen content of the molten aluminum affects the porosity of castings made therefrom. Due to a large difference between the solubility of hydrogen in liquid and in solid aluminum, dissolved hydrogen precipitates from the melt during solidification and becomes trapped in the castings. Accordingly, it is essential to monitor the hydrogen level of the melt before the metal is cast to determine if hydrogen removal is necessary. Techniques used heretofore to measure hydrogen content are generally too slow for a practical commercial application. Attempts have been made to develop solid state electrochemical sensors for the rapid on-site determination of hydrogen content. Such sensors employ a solid electrolyte comprising calcium hydride and a reference electrode comprising a mixture of calcium and calcium hydride. The sensor is immersed in the molten aluminum such that the electrolyte comes into direct contact with the melt and a concentration cell is established between the hydrogen partial pressure in the reference electrode and the hydrogen partial pressure in the melt. Such sensors, however, are short lived due to instability of the calcium hydride electrolyte in contact with the melt.

It is an object of the present invention to provide an improved long-lived, responsive, solid-state hydrogen sensor which includes means for isolating the electrolyte from the aluminum melt, for measuring the hydrogen partial pressure in gas phase equilibrium with the melt, and for catalyzing the hydrogen exchange reaction.

This and other objects and advantages of the present invention will become more readily apparent from the detailed description thereof which follows and which is given hereafter in conjunction with the Figures in which.

BRIEF DESCRIPTION OF THE INVENTION

The sensor of the present invention takes the form of a probe comprising: (1) a hydrogen electrode including a catalytic metal membrane which is selectively permeable to the passage of hydrogen therethrough; (2) a counterelectrode comprising a mixture of calcium and calcium hydride wherein the calcium hydride is sufficient in amount to provide a predetermined reference hydrogen partial pressure at the temperature of the molten aluminum; (3) a solid state electrolyte interjacent the electrode and counterelectrode and comprising a hydrogen ion conducting material selected from the group consisting of calcium hydride, calcium hydrochloride and strontium hydrochloride; and (4) a porous barrier for separating the hydrogen electrode from direct contact with the melt and for forming a hydrogen gas collection chamber contiguous the hydrogen electrode. The porous barrier comprises a porous material which has pores sufficiently large as to be readily permeable by hydrogen yet sufficiently small as to be impermeable by the melt. In accordance with one embodiment, hydrogen diffusing from the melt passes through the pores of the porous barrier into the collection chamber and into contact with the hydrogen electrode. In accordance with another embodiment, the chamber is precharged with hydrogen and some of the precharge exits the chamber and diffuses into the melt. In either case the chamber holds the hydrogen therein at a partial pressure in substantial equilibrium with the melt on the other side of the porous barrier. Appropriate electrical leads (e.g., wires) extend from the hydrogen electrode and the counterelectrode to a voltmeter, or the like, which is responsive to the difference in electrical potential established between the electrode and the counterelectrode incident any difference between the reference and equilibrium partial pressures of the hydrogen in accordance with well known concentration cell principles.

The hydrogen electrode comprises a metal membrane which is effective to catalyze the hydrogen exchange reaction and which is selectively permeable to hydrogen and hence will comprise palladium (i.e., about 0.1 mm thick) platinum coated (i.e., sputtered) iron or similar materials. The porous barrier will preferably have the largest pore diameters possible consistent with exclusion of melt therefrom, will vary with the composition, temperature and head of the molten metal as well as the composition of the barrier itself. The larger pore sizes are preferred in order to achieve the most rapid diffusion of the hydrogen from the melt and hence a more responsive probe. Tests have been successfully run with boron nitride barriers having pore diameters of about 0.030 inch but somewhat larger pores are believed possible. Perforated discs or porous plugs of the type used to chloride molten aluminum are acceptable forms of porous barriers for the present application.

DETAILED DESCRIPTION OF A SPECIFIC EMBODIMENT

Figure 1:
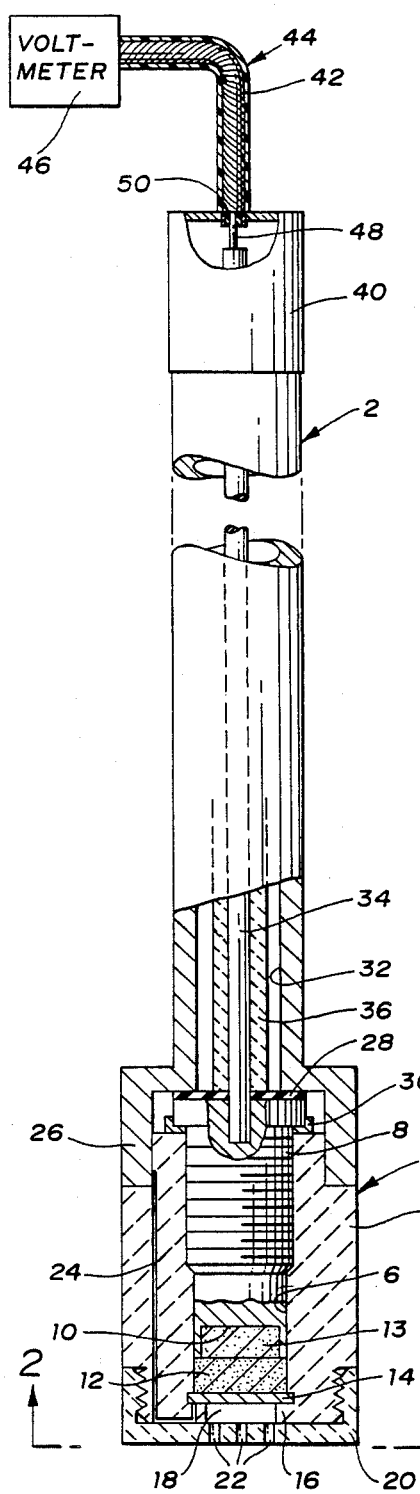
FIG. 1 is a partially broken away and sectioned elevational view of a probe in accordance with the present invention.
Figure 2:
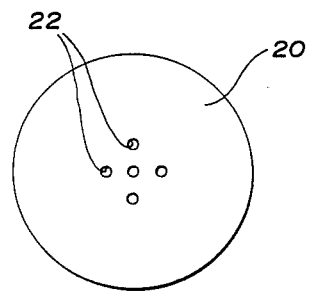
FIG. 2 is a view in the direction 2—2 of FIG. 1.

FIGS. 1 and 2 show a probe 2 having a sensor head 3 comprising a nonconductive housing 4 which is substantially chemically inert to the molten aluminum and which preferably comprises boron nitride. The housing 4 has a central bore 6 therein receiving threaded molybdenum insert 8 screwed thereinto. The insert 8 includes a cavity 10 in the end thereof packed full of a counterelectrode mixture 13 of calcium and calcium hydride. The mixture 13 is positioned contiguous a pellet 12 of calcium hydride pressed into place in the bore 6 atop a palladium membrane 14 (i.e., 0.1 mm thick) resting on the annular shoulder 16 which, in turn, defines a chamber 18 for holding the gaseous hydrogen to be measured in contact with the palladium membrane 14. A boron nitride cap 20 is screwed onto the end of the boron nitride housing 4 and includes a plurality of 0.030 inch diameter bores 22 therein to permit hydrogen diffusing out of the molten aluminum to enter the hydrogen chamber 18 while, at the same time, preventing molten aluminum from invading the chamber 18 and contacting the membrane 14. A metal (e.g., molybdenum) wire 24 connects the palladium membrane 14 to a tubular steel shaft 26 which carries the housing 4. An insulating gasket 28 seals and insulates the insert 8 from the carrier 26 while a Graphoil ® gasket 30 prevents hydrogen from escaping from the cavity 6 up the hollow center 32 of the tubular shaft 26. A steel rod 34 encased in a protective ceramic sheath 36 extends through the hollow center 32 of the shaft 26 to engage the insert 8 and serve as the primary electrical lead therefrom. A metal cap 40 closes off the upper end of the shaft 26 and provides electrical continuity to the outer conductor 42 of a coaxial cable 44 which extends to a voltmeter 46 which is responsive to the difference in potential between the electrode 14 and counterelectrode 13 resulting from the difference in hydrogen partial pressures in the cavity 10 and the chamber 18. The center conductor 48 of the coaxial cable 44 is insulated from the outer conductor 42 by insulating material 50 and contacts the steel rod 34 electrically connected to the counterelectrode 13 via insert 8.

In operation, the probe is immersed into an aluminum melt and left there for a time sufficient for the probe to be heated to the temperature of the melt and for the hydrogen in the chamber 18 to come into equilibrium with the melt. At that time, decomposition of the calcium hydride in the counterelectrode calcium/calcium hydride mix 13 establishes a known hydrogen partial pressure in the cavity 10 which is a function only of the temperature of the melt. The partial pressure is known to be independent of composition (i.e., in the range 20 to 90 weight percent $CaH_2$) and remains constant at a given temperature.

After the probe has achieved steady state in the melt, the potential between the electrode and counterelectrode is measured by the voltmeter 46. In this regard, the cell potential (E) is given by the relation $$E = -\frac{RT}{2F} \ln \frac{P'_{H2}}{P_{H2}} \quad [1]$$

where $P'_{H2}$ and $P_{H2}$ are the partial pressures for hydrogen associated with the reference mixture 13 and the hydrogen chamber 18, respectively. R, T, and F are, respectively, the gas constant, temperature in Kelvin, and the Faraday constant.

The partial pressure of hydrogen associated with the ($Ca+CaH_2$) mixture 13 is independent of composition between 20 to 90 weight percent $CaH_2$, remains constant at a given temperature, and is expressed as $$\log P'_{H2} = -\frac{A}{T} + B. \quad [2]$$

The values of the constants A and B have been experimentally evaluated by several investigators such as R. W. Curtis and P. Chiotti, J. Phys. Chem, 67, (1963), 1061-65; W. D. Treadwell and J. Sticher, Helv. Chem. Acta, 36, (1957), 1820-32; and W. C. Johnson, M. F. Stubbs, A. E. Sidwell and A. Peahukas, J. Am. Chem. Soc., 61, (1939), 318-29. Since the value of $P'_{H2}$ is constant at a given temperature, Equation [1] may be expressed as $$E = -\frac{RT}{2F} \ln P_{H2} + \text{constant} \quad [3]$$

at given temperature, yielding a simpler relation between the cell potential and the partial pressure of hydrogen to be determined.

Testing

Figure 3:
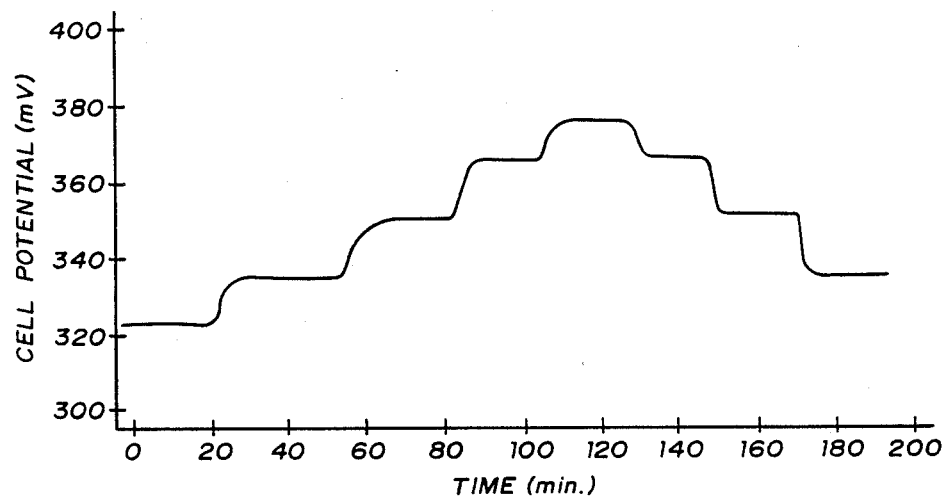
FIG. 3 is a plot of the sensor's response to changes in hydrogen content of a test gas exposed thereto.
Figure 4:
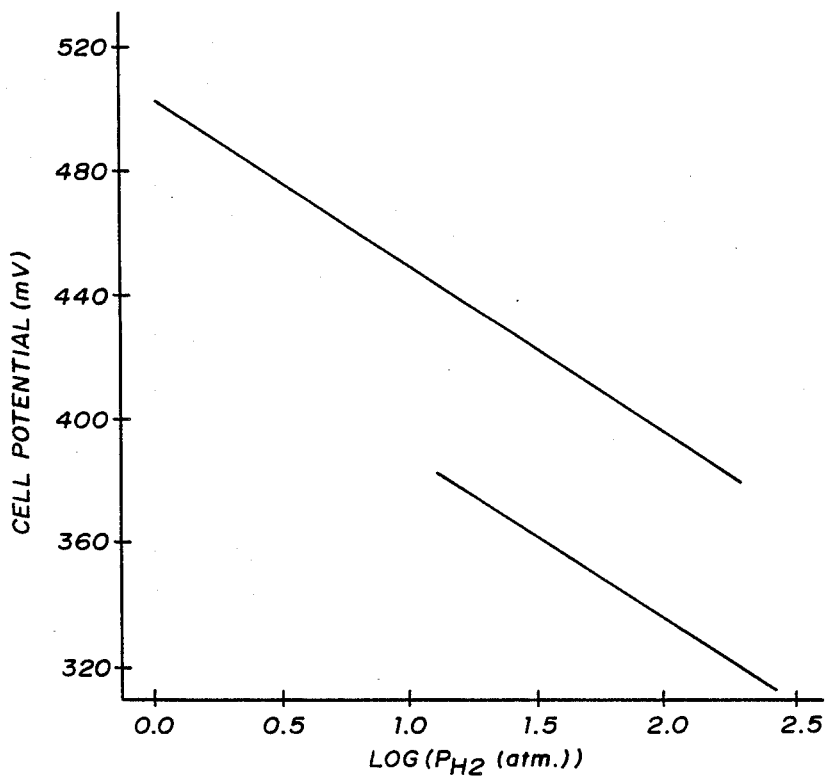
FIG. 4 is a plot of the sensor's output (i.e., cell potential) as a function of hydrogen partial pressure in a test gas.

Several versions of the sensor were built essentially as described above and were tested at various temperatures and in essentially helium having hydrogen partial pressures which varied between $4.97 \times 10^{-3}$ atmospheres to about $5.66 \times 10^{-2}$ atmospheres The sensor's response was found to be rapid and reversible with change in hydrogen partial pressure, as shown in FIG. 3 which plots the voltage developed by the probe at different hydrogen pressures at 350° C. over a 200 minute test period. Moreover, as shown in FIG. 4, the cell potential was shown to vary linearly and reversibly with the logarithm of hydrogen pressure at a given temperature (i.e., 305° C. and 350° C. shown).

While the invention has been disclosed primarily in terms of specific embodiments thereof it is not intended to be limited thereto but rather only to the extent set forth hereafter in the claims which follows.

The embodiments of the invention in which an exclusive property or privilege is claimed are defined as follows:

1. A probe adapted for immersion into a melt of aluminum for responsively electrochemically determining the hydrogen concentration in said melt comprising:

a hydrogen electrode comprising a catalytic metal membrane selectively permeable to the passage of hydrogen therethrough;

a counterelectrode comprising a mixture of calcium and sufficient calcium hydride to provide a predetermined reference hydrogen partial pressure at the temperature of said melt;

a solid state electrolyte interjacent said electrode and said counterelectrode and selected from the group consisting of calcium hydride, calcium hydrochloride and strontium hydrochloride;

a hydrogen accumulation chamber adjacent said membrane for holding gaseous hydrogen at a partial pressure in substantial equilibrium with the hydrogen in said melt;

porous barrier means interjacent said chamber and said melt for separating said hydrogen electrode from deleterious contact with said melt and establishing a gas-liquid interface between said melt an said gaseous hydrogen in said chamber, said barrier means having pores sufficiently small as to prevent said melt from passing therethrough yet sufficiently large as to readily permit hydrogen to pass therethrough; and electrical contact means extending from said electrode and counterelectrode for coupling to a hydrogen concentration indicator means responsive to the difference in electrical potential established between said electrode and said counterelectrode incident to the difference between said reference and equilibrium partial pressure.

2. A probe according to claim 1 wherein said pores have a diameter of at least about 0.030 inch.

3. A probe according to claim 1 wherein said chamber comprises pores in said barrier between said melt and said membrane.

4. In a probe for responsively electrochemically measuring the hydrogen concentration in an aluminum melt wherein said probe includes principally a reference electrode comprising a mixture of calcium and calcium hydride and a solid state electrolyte comprising calcium hydride the improvement comprising:

a hydrogen electrode comprising a catalytic metal membrane selectively permeable to the passage of hydrogen therethrough;

a hydrogen accumulation chamber adjacent said membrane for holding gaseous hydrogen at a partial pressure in substantial equilibrium with the hydrogen in said melt; and porous means permeable to hydrogen and substantially impermeable to said melt for separating said hydrogen electrode from deleterious contact with said melt while maintaining a gas-liquid interface between said melt and said gaseous hydrogen in said chamber.

* * * * *